United States Patent
Dixon et al.

(10) Patent No.: US 6,709,438 B2
(45) Date of Patent: Mar. 23, 2004

(54) CAM ACTION VERTEBRAL SPREADER

(76) Inventors: Robert A Dixon, 10577 Durham Pl., Powell, OH (US) 43065; Donald J Hackman, 3499 Kirkham Rd., Columbus, OH (US) 43221

( * ) Notice: Subject to any disclaimer, the term of this patent is extended or adjusted under 35 U.S.C. 154(b) by 111 days.

(21) Appl. No.: 09/923,063

(22) Filed: Aug. 6, 2001

(65) Prior Publication Data

US 2002/0026191 A1 Feb. 28, 2002

Related U.S. Application Data

(60) Provisional application No. 60/224,472, filed on Aug. 10, 2000.

(51) Int. Cl.[7] ............................................... A61B 17/66
(52) U.S. Cl. ....................................................... 606/90
(58) Field of Search .............................. 606/86, 90, 96, 606/99

(56) References Cited

U.S. PATENT DOCUMENTS

| | | | |
|---|---|---|---|
| 5,484,437 A | | 1/1996 | Michelson |
| 5,697,977 A | * | 12/1997 | Pisharodi ..................... 606/61 |
| 5,755,732 A | * | 5/1998 | Green et al. ................ 606/170 |
| 5,797,909 A | | 8/1998 | Michelson |
| 5,899,908 A | | 5/1999 | Kuslich et al. |
| 6,030,390 A | * | 2/2000 | Mehdizadeh .................. 606/84 |
| 6,080,155 A | | 6/2000 | Michelson |
| 6,277,122 B1 | * | 8/2001 | McGahan et al. ............. 606/90 |
| 6,290,724 B1 | * | 9/2001 | Marino ..................... 623/17.11 |
| D458,372 S | * | 6/2002 | Dixon et al. ................ D24/147 |
| 2002/0010473 A1 | * | 1/2002 | Lin ............................... 606/99 |

OTHER PUBLICATIONS

PRECISION–GRAFT (TM), MEDTRONIC SOFAMOR DANEK, MEMPHIS TN (brochure).

* cited by examiner

Primary Examiner—Kevin Shaver
Assistant Examiner—Michael B. Priddy

(57) ABSTRACT

This invention comprises an apparatus and a method of spreading an intervertebral space to help guide tools that will prepare the vertebrae for accepting an implant. The spreader is a thin blade with cam surfaces forming a paddle on the proximal end, which spreads the vertebra when rotated 90 degrees about its axis. A stem between the paddle and a handle is notched to clear the vertebral protrusions so the vertebra will be distracted on the vertebral end plates. Since the spreader is in the center of the end plates, the centerline of the spreader shaft will coincide with the vertebral end plate centerline. The surgeon can monitor the spreading, stop and remove the spreader to make adjustments or to change the size of spreader as required at the time of the surgery. Once the vertebrae are distracted a tube may be placed over the handle and aligned with the vertebral end plates.

3 Claims, 4 Drawing Sheets

CAM ACTION VERTEBRAL SPREADER

CROSS-REFERENCES TO RELATED APPLICATIONS

This patent application was preceded by: Provisional Patent No. 60/224,472 with a file date of Aug. 10, 2000

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

Spinal fusions are performed to treat degenerative diseases, deformities, and trauma. These problems generally cause or allow displacement or rotation of a vertebra relative to the adjacent vertebra. The objective of spinal implants is to facilitate realignment and/or fixation of spinal elements for fusion. It has been demonstrated in clinical studies, that surgeries using spinal implants are more effective at providing structure and rigidity to the spine than surgeries in which implants are not used.

The majority of existing spinal implants use metal rods or plates to restrict the relative motion of the adjacent vertebra while fusing. Once the two vertebrae are fused there is no longer a need for the rods or plates, which may later cause complications. Certain implants are absorbed leaving no foreign material. Implant placement and success can be improved by use of distracting or spreading to stretch the attaching ligaments. This stretching of the ligaments is called ligamentotaxis. Ligamentotaxis is used by surgeons to restore the anatomic alignment of the spine, help to maintain the spinal implant in the proper position, and encourage graft incorporation by loading the graft host interface. This patent provides for an improved method and device for the purpose of spreading spinal elements such as vertebrae to accept spinal implants.

DESCRIPTION OF PRIOR ART

A bone fusion, using a threaded cylindrical dowel bone implant, may be performed between two adjacent vertebrae to restore the space originally occupied by a disc. To increase the surface area of contact between the flat vertebral end plates and the cylindrical dowel or the absorbable fixation screw surface, it is necessary to prepare the flat vertebral end plates to a partial cylindrical concave surface.

U.S. Pat. No. 6,080,155 to Michelson is an example of a hollow tube 64 with two protruding tangs 60, shown in FIG. 12, are used for distraction. These tangs are referred to in the literature as extended outer sleeves 64. These tangs are hammered into the disc space to force distraction. Since the tangs are tapered 61, any movement of the tube causes a component of the holding force to tend to dislodge the sleeve. Because of the misalignment angle 63, the tangs do not hold the tube reliably and they allow trapezoidal deformation, especially with the cervical vertebrae, which are smaller than the lumbar vertebrae. U.S. Pat. No. 5,899,908 to Kuslich et al. is an example of cylindrical plug 70 with a bullet nose 71 is used for distraction. The cylindrical distractor is hammered into place by shaft 72. The tangs or cylindrical plugs distract and lift the vertebra by contacting it on the edges at the vertebral protrusions 27. This moves the distractor centerline away from the end plate centerline therefore the end plates are not distracted parallel. The tangs are short compared to the tube length. This results in an unstable tube position during the reaming and tapping procedures.

Another method uses circular tangs 61, which centers on the vertebral end plates as shown in FIG. 13. However to force the dual circular tangs through the intervertebral space requires extreme over distraction as the tang distracts the protrusion 62. This would cause trauma to the vertebrae as well as the tethering ligaments. Once in place the tube is used to guide a sleeve, a reamer, and a thread tap. After the machining is completed the bone dowel can be guided through the tube for implantation.

SUMMARY OF THE INVENTION

The purpose of the present invention is to provide a device and a method to distract the flat surfaces on the intervertebral end plates to receive an implant. This device comprises a vertebral cam spreader as shown in various embodiments in the subsequent drawings. The vertebral end plates are spread with the cam spreader appliance in a controlled fashion. The spreader cam is positioned at the center of the vertebral end plates with the spreader in a flat or horizontal position. The cam sections are extended past the vertebral protrusions before beginning to spread the vertebrae. This will provide a controlled uniform spreading, without over spreading, and assure a controlled uniform spacing of the vertebrae. Since the spreader is in the center of the end plates, the centerline of the spreader shaft will coincide with the vertebral end plate centerline. The surgeon can monitor the spreading and can stop and remove the spreader to make adjustments or to change the size of spreader as required at the time of the operation. This cam spreader eliminates the traumatic stress caused by hammering tangs or other distraction devices into place. The disc need not be removed.

The degree of lordosis may be altered by changing the depth of the cam spreader. Various tools can then be attached to or around the cam spread to remove the necessary sections of the disc or vertebrae. For instance, once the vertebrae are spread, a tube with holding tabs is placed over the spreader shaft. The spreader has centering means that will insure that the tube is concentric with the spreader. When the tube is in place, bone screws can be placed through the tabs and into the adjacent vertebra to maintain the vertebral relative position while the tooling and implant are in use. The tube assures that the tools will be centered on and parallel to the vertebral end plates. This in turn can facilitate removing an appropriate amount of material from each adjacent vertebra. After the machining is completed the bone dowel can be guided through the tube and be contained in place with a holding means, preferably a screw thread. These machining and dowel insertion operations are well known to those skilled in the art.

OBJECTS OF THE PRESENT INVENTION

An object of the present invention is to provide a spreader that will distract two vertebrae to place them into preferred positions without over distracting during the process.

Another object of the present invention is to provide an improved method and device for preparing vertebrae for a discectomy, a fusion, and for spinal stabilization.

Another object of the present invention is to provide a method of performing a fusion safer, easier, and in less time than in prior art.

Another object of the present invention is to provide an improved device and a method of performing a spinal fusion and a spinal stabilization using harvested bone, absorbable implants and dowels and metal or nonmetal implants.

Another object of the present invention is to provide devices and methods for cervical, thoracic, and lumbar spinal fusions anteriorly, posteriorly, and/or laterally.

A further object of the present invention is to provide a means for inserting a spinal implant between adjacent vertebrae, while maintaining their optimal spacing, positioning, and alignment.

DETAILED DESCRIPTION OF THE INVENTION

Figure 1:
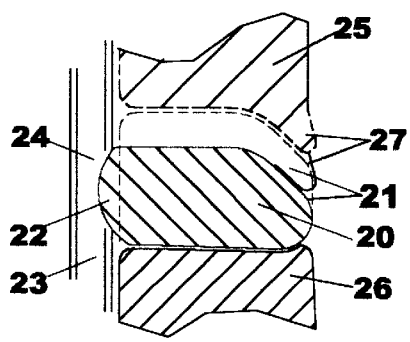
FIG. 1 is a side section view of a herniated intervertebral disk collapsed causing spinal compression stenosis, taken along the line 1—1 of FIG. 2.
Figure 2:
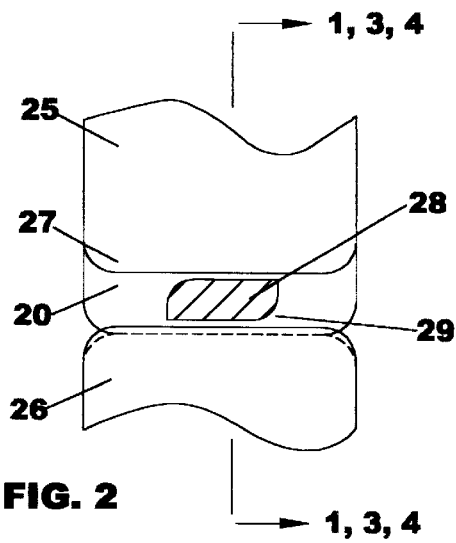
FIG. 2 is a ventral view of a collapsed disc with the vertebral spreader inserted into the disc.
Figure 3:
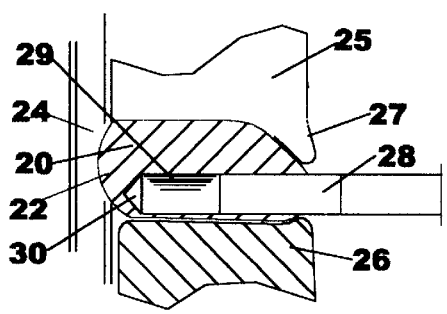
FIG. 3 is a side section view of a preferred embodiment of a vertebral spreader inserted into a collapsed disc, taken along the line 3—3 of FIG. 2.

It is understood that words like "upper" and "lower", do not imply specific direction or placement, but are used only for convenience to describe the device. In the description upper refers to the vertebra nearer to the patients head and lower refers to the vertebra nearer the patients feet. It is also understood that "fixed" and "rigid" are relative terms not implying zero measurable motion, but much less motion relative to the adjacent vertebra before installation of the stabilizer system. For simplification the vertebral cam spreader is described in one of many conceivable embodiments. The vertebral cam spreader may be referred to as the 'device'. That is not to imply that this is the only embodiment within which the device can be configured. The components may be fabricated from metal, preferably titanium or a titanium alloy The Device The Herniated Disc A normal disc 21 is shown with a dashed line in FIG. 1. When spinal discs rupture or bulge 20 from injury or from degeneration, the space between two adjacent vertebra 25 and 26 decreases. Frequently the bulging 22 does no harm, but if it compresses 24 against the spinal cord 23 or a nerve it may cause pain, loss of sensation, or weakness. Spinal compression 24 is shown in FIG. 1. In these situations, when surgery is indicated, it is generally safer to replace the disc with a rigid implant and accept the loss of motion that the disc once provided. The vertebral protrusion may be an obstacle to implant insertion and may have to be removed. The process of removing a disc and replace it with a rigid implant is referred to as fusing.

The Vertebral Cam Spreader

Figure 4:
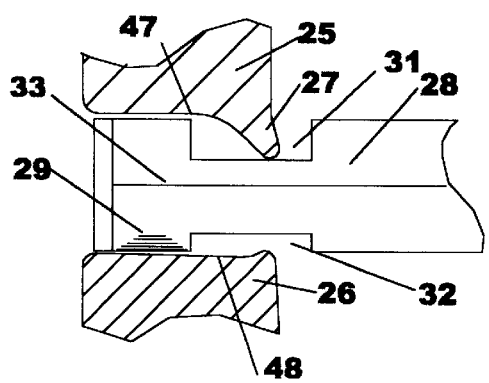
FIG. 4 is a side section view of a vertebral disk spreader inserted into the collapsed disc and rotated 90 degrees to spread two adjacent vertebrae, restoring the space, taken along the line 4—4 of FIG. 2.
Figure 5:
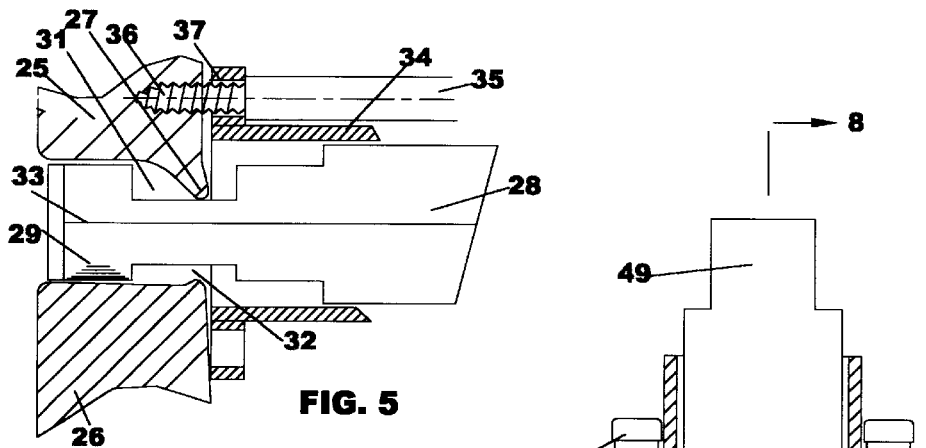
FIG. 5 is a side section view of a vertebral disc, with the spreader rotated to restore the collapsed disc space, along line 5—5 of FIG. 7. The alignment tube is attached with bone screws.

As shown in FIGS. 2, 3, 4, and 5 the spreader is a thin blade 28 with cam surfaces 29 which spread the vertebrae, when rotated 90 degrees as shown in FIGS. 4 and 5, to allow for preparation and implantation between two adjacent vertebra. The distal end of the spreader may have a knife-edge 30 to aid in removing or separating the disc and facilitating the placement of the spreader. The spreader has clearance notches 31 and 32, which allow the cam surfaces 29 to spread the vertebra from the end plates 47 and 48 rather than from the lip 27 as in the prior art. The vertebral end plates are spread with the cam spreader appliance 28 in a controlled rotation. The spreader cams 29 are positioned at the center of the vertebral end plates 47 and 48 when rotated, assuring even uniform spacing of the distracted vertebra. The device may have a drive extension 49 to attach a rotating means such as a "T" handle. Since the spreader is in the center of the end plates, the centerline of the spreader shaft will coincide with the vertebral end plate centerline. The surgeon can monitor the spreading, stop and remove the spreader to make adjustments or to change the size of spreader as required at the time of the surgery. The clearance notches allow clearance of vertebral prominence or spurs. These notches provide for more accurate positioning of the end-plates in the distracted position for subsequent machining.

The Guide Tube

Figure 7:
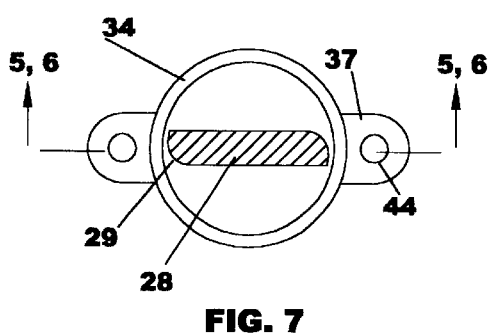
FIG. 7 is an end view of the tube and spreader take along the line 7—7 of FIG. 6.
Figure 6:
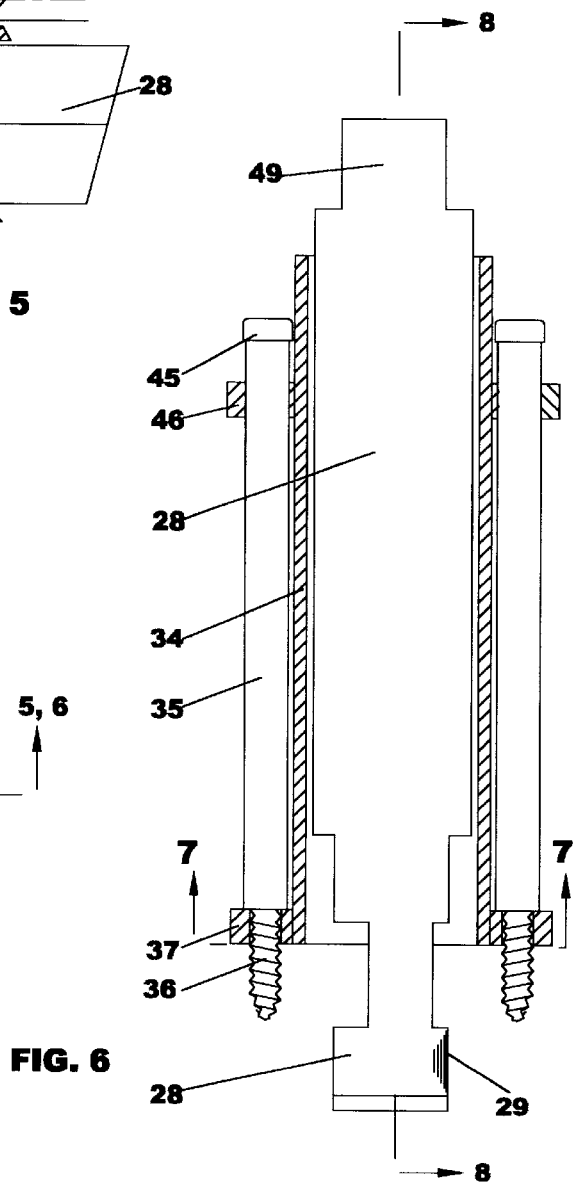
FIG. 6 is a side sectional view of the entire length of the spreader, tube and screws taken along line 6—6 of FIG. 7.
Figure 8:
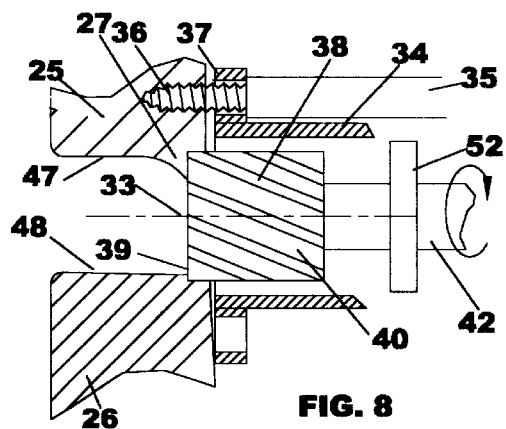
FIG. 8 is a side view of the reamer cutting the vertebra taken along the line 8—8 of FIG. 6.
Figure 9:
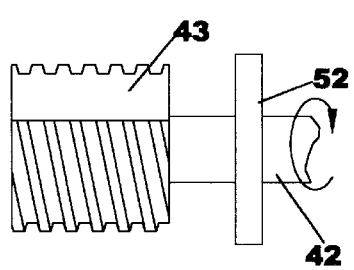
FIG. 9 is a side view of the thread tap.
Figure 11:
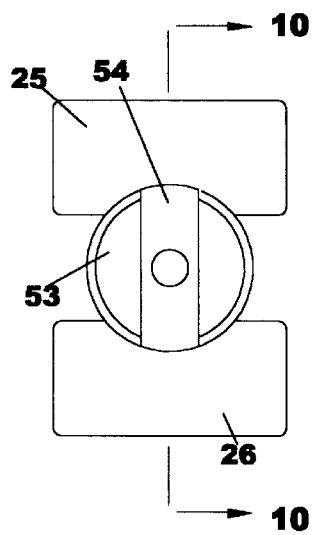
FIG. 11 is an end view of the implant looking in the direction, taken along line 11—11 of FIG. 10.
Figure 12:
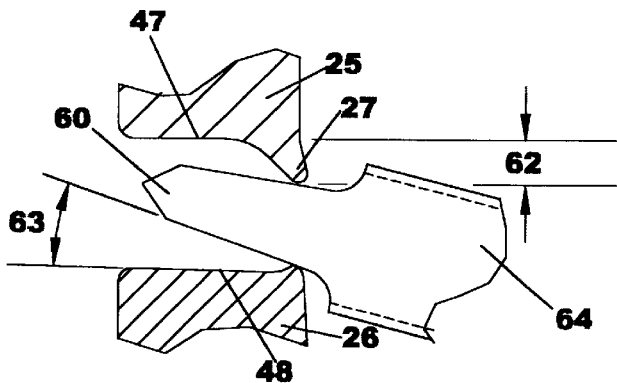
FIG. 12 is a side view of a prior art tube with a tapered tang with the vertebrae shown in section.
Figure 13:
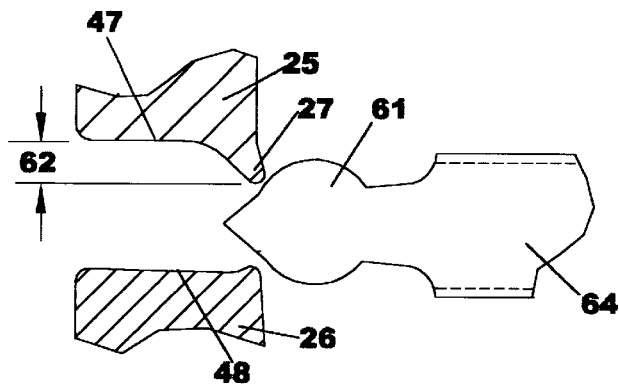
FIG. 13 is a side view of a prior art tube with a circular disk distractor with the vertebrae shown in section.
Figure 14:
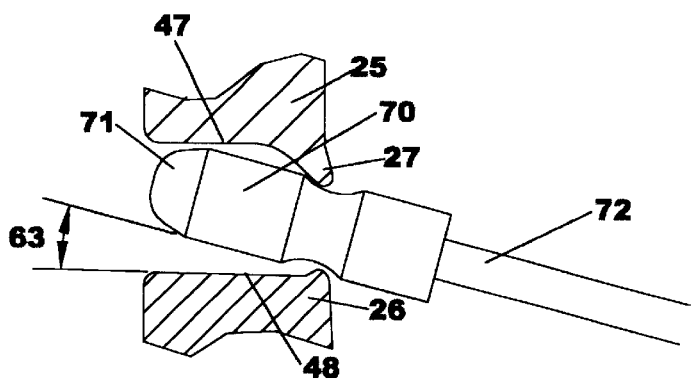
FIG. 14 is a side view of a prior art cylindrical plug distractor with the vertebrae shown in section.

Once the vertebrae are spread, a guide tube 34, shown in FIGS. 5, 6, and 7 is placed over the spreader stem 28. The spreader has centering means that will insure that the tube is concentric with the spreader 28. After the tube 34 is in place, two screws 36 can be placed through the holes 44 in tabs 37 and threaded into the adjacent vertebra 25 and 26 to maintain the vertebra's relative position while the tooling and implanting operations are taking place. Screw extensions 35 may be held in position by guide holes 46. The screw is driven by the head 45. The cam spreader 28 can be removed to allow the tools to be guided into place. The tube also assures that the tools 40 and 43 in FIGS. 8 and 9, will be centered on the vertebral end plates 47 and 48 and parallel to the end plate to facilitate removing an appropriate amount from each adjacent vertebra. The machining tools and implant are inserted through the tube 34. The guide tube may be used as a working channel for decompression.

The Vertebra Machining Tools

The tools 40 and 43 are aligned with the tube 34 with centering disk 52 on shaft 42. This assures that the tools 40 and 43 in FIGS. 8 and 9 will be centered on and parallel to the vertebral end plates 47 and 48. A drill or a reamer 40 is used to machine the fusing surfaces to prepare for threading the vertebral end plates 47 and 48. The tool guidance tube 34 facilitates removing an appropriate amount from each adjacent vertebra 25 and 26. After the surfaces are machined to the proper size and surface finish, a threading tap 43, which will accommodate the selected implant, will cut the internal thread. The machining tools and the implant can then be inserted through the tube 34. The spreading cam 28 must be removed to allow the tools to be guided into place leaving the screws 36 and the tube structure 34 to maintain the vertebral space. The reaming, tapping, and implant insertion operations are well known to those skilled in the art.

A reamer with a flat cutting end 39 and edge of the cutting circumferential lands 38 is preferred over a drill because a drill point angle has a radial force component that tends to spread the vertebrae 25 and 26, producing an uneven cut. The reamer 40 also removes the section of the vertebral protrusion 27, which in prior art, interfered with full-length implant contact.

The Implant

Figure 10:
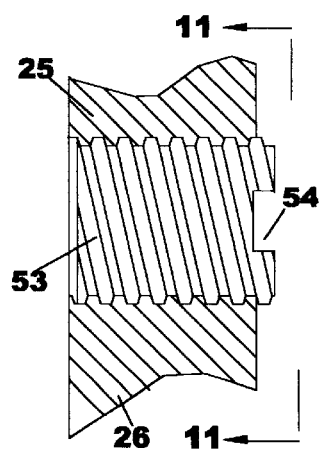
FIG. 10 is a side section view of the implant taken along the line 10—10 of FIG. 11.

After the machining is completed, an implant, preferably a bone dowel 53, can be guided through the tube and threaded into place with a purpose built screwdriver or other installation means inserted in slot 54. The implant may also be fabricated differently to accommodate other driving or inserting means. The implant may have other features that will hold it to the driving device as it is being manipulated into position for insertion. The preferred embodiment shows a bone screw 53 in FIG. 10 to be implanted for bone fusion across an intervertebral space, following the removal of a damaged disc. Such implants are structurally load-bearing devices, capable of withstanding the forces supported by the upper vertebra 25. The implant of the present invention has a thread to maintain the position. The implant 53 must be in contact with the circular arcs machined in the vertebral end plates 47 and 48. The implant may be fabricated from metal, preferably titanium or a titanium alloy. The implant may also be fabricated from other metals, nonmetals, polymers, biodegradable materials, bioabsorbable materials, and allograft or autograft materials.

The Method

The spreader cam 28 in FIGS. 4 and 5 is positioned at the center of the vertebral end plates 47 and 48 and is rotated to spread the vertebrae. The cams 29 assure even uniform spacing. The spreader is positioned in the center of the end plates; the centerline 33 of the spreader shaft 28 will coincide and overlap with the vertebral end plates midway between the end plates. The surgeon can monitor the spreading and can stop and remove the spreader, to make adjustments or to change the size of spreader, as required at the time of the operation. The disc may not need to be removed, since the spreader 28 and the reamer 40 will remove any material that is within their respective machining paths. The cam spreader shaft may be advanced, with a mallet, into the vertebral endplates to facilitate removal for posterior or lateral approaches.

Once the vertebrae are spread, a tube 34 with, holding tabs 37, is placed over the spreader shaft 28. The spreader has centering means that will insure that it is concentric with the guide tube spreader. When the tube 34 is in place, bone screws 36 may be placed through the tabs and into the adjacent vertebra to maintain the vertebrae relative position while the tooling 40 and 43 and implant insertion are in use. At the surgeon's option, a starting hole may be drilled in the vertebra, prior to threading the guide tube screws 36 into the vertebra 25 and 26. This starting hole, also referred to as a tap drill, will reduce the screw tightening torque in the vertebra. The tube assures that the tools will be centered on and parallel to the vertebral end plates 47 and 48.

The reamer 40 is inserted into the guide tube 34 to locate it with respect to the vertebrae. This alignment will assure that an equal amount of circular arc is removed from each adjacent vertebra. After the arcs are machined they may be tapped with an internal thread to allow the implant 53 to be held in position while the bones fuse together. A stop is used on the tool shafts to set the depth of the implant as well as the tools. After the machining is completed the bone dowel 53 can be guided through the tube 34 and be contained in place with a holding means, preferably a screw thread 53. The implant is inserted through the tube, and tightened with a screwdriver or other means. These machining and dowel insertion operations are well known to those skilled in the art.

We claim:

1. A bone segment spreader for temporarily increasing the space between two adjacent bone segments, for preparation and implantation of a graft, said graft acting as a spacer between said bone segments, said bone segments having hard end plates and protrusions, said protrusions interfering with access to said hard end plates, said bone segment spreader comprising:

(a) an elongated one piece thin blade having a longitudinal axis, an upper surface, a lower surface, a distal end, and a proximal end; and (b) said thin blade further having a cam spreader portion at said distal end, said cam spreader serving to bear upon said end plates and increase said space between said bone segments when said spreader is inserted and rotated about said axis; and (c) a stem driving portion at the said proximal end of said blade, said stem driving portion to facilitate insertion, rotation, and removal of said bone segment spreader; and (d) said thin blade also having a clearance notch portion, with individual notches, positioned between said cam spreader portion and said stem driving portion, said individual notches providing clearance for said bone protrusions when the bone spreader is rotated about said axis.

2. The device of claim 1, wherein the said spreader portion has a knife edge at said distal end to facilitate passage of a portion of said bone spreader into said space between said bone segments.

3. A method for spreading said adjacent bone segments, comprising:

providing the bone segment spreader of claim 1;

sliding said bone segment spreader into said space between said adjacent bone segments with the said upper and lower surfaces of said thin blade parallel to and adjacent to said end plates;

rotating said spreader ¼ turn about said axis to spread said adjacent bone segments for implantation of said graft into said space;

rotating said spreader an additional ¼ turn;

removing said spreader out of said space.

\* \* \* \* \*